United States Patent [19]
Picolet et al.

[11] Patent Number: 4,492,225
[45] Date of Patent: Jan. 8, 1985

[54] CRADLES AND MINERVA JACKETS, AND MANUFACTURING MATERIAL THEREFOR

[75] Inventors: Jean-Pierre Picolet, St Priest-en-Jarez; Jean-Loup Rudloff, Nanterre; François Courtet, St Bonnet-les-Oules, all of France

[73] Assignees: Etablissements Thuasne & Cie; Thuasne-Paris, both of France

[21] Appl. No.: 448,995

[22] PCT Filed: Feb. 19, 1982

[86] PCT No.: PCT/FR82/00030
§ 371 Date: Nov. 9, 1982
§ 102(e) Date: Nov. 9, 1982

[87] PCT Pub. No.: WO82/03005
PCT Pub. Date: Sep. 16, 1982

[30] Foreign Application Priority Data
Mar. 10, 1981 [FR] France ............... 81 04715

[51] Int. Cl.³ .................................................. A61F 5/04
[52] U.S. Cl. ............................... 128/87 R; 128/89 R
[58] Field of Search ................. 128/87 R, 89 R, 90, 128/155, 156, 133, 134

[56] References Cited

U.S. PATENT DOCUMENTS

| | | | |
|---|---|---|---|
| 2,933,083 | 4/1960 | Kozdas | 128/89 R |
| 3,942,522 | 3/1976 | Wilson | 128/90 |
| 4,161,175 | 7/1979 | Bentele | 128/87 A |
| 4,211,218 | 7/1980 | Kendrick | 128/87 R |
| 4,274,402 | 6/1981 | Shippert | 128/89 R |

Primary Examiner—John D. Yasko
Attorney, Agent, or Firm—Peter L. Berger

[57] ABSTRACT

Material for manufacturing articles for supporting the head or members of persons or animals, and articles manufactured from such material. The material is characterized in that it consists of a layered panel formed by the assembly of a plastic material layer in the form of hard foam, a preferably non elastic metal sheet, a plastic material layer in the form of a flexible foam, and a smooth and flexible protective inner sheet.

17 Claims, 14 Drawing Figures

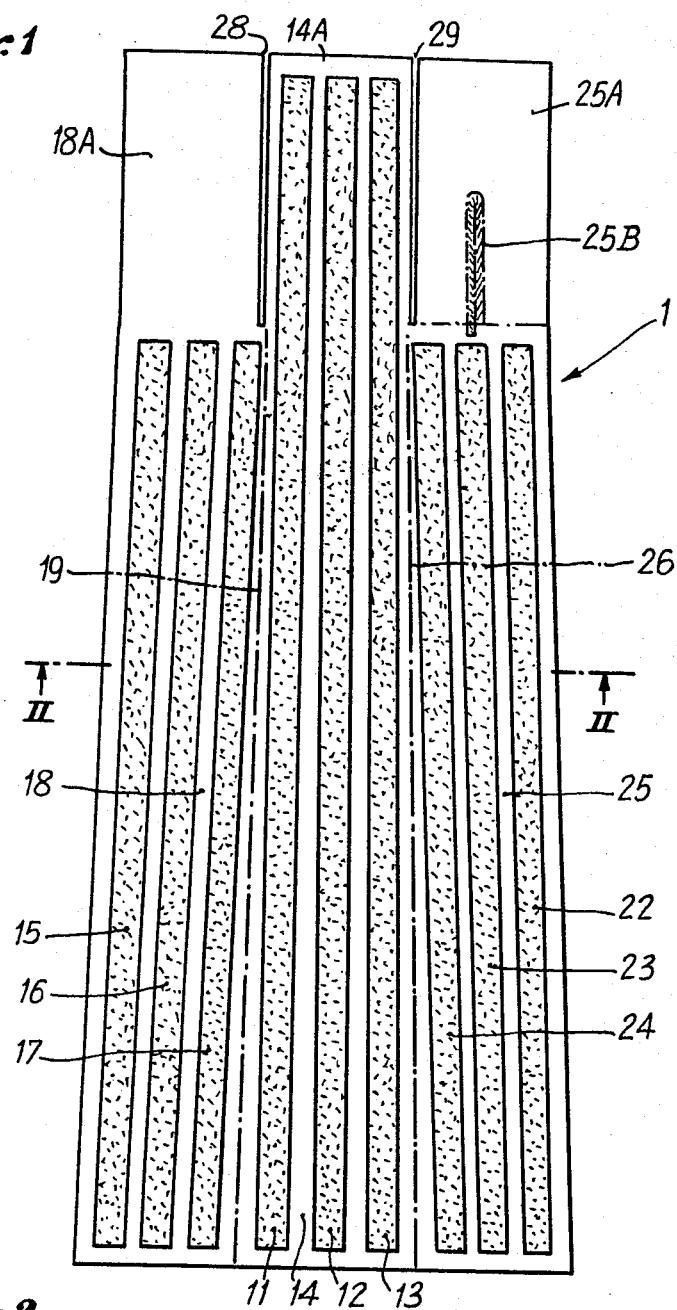
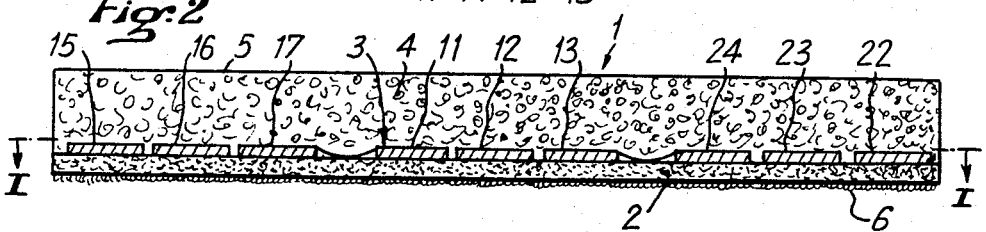

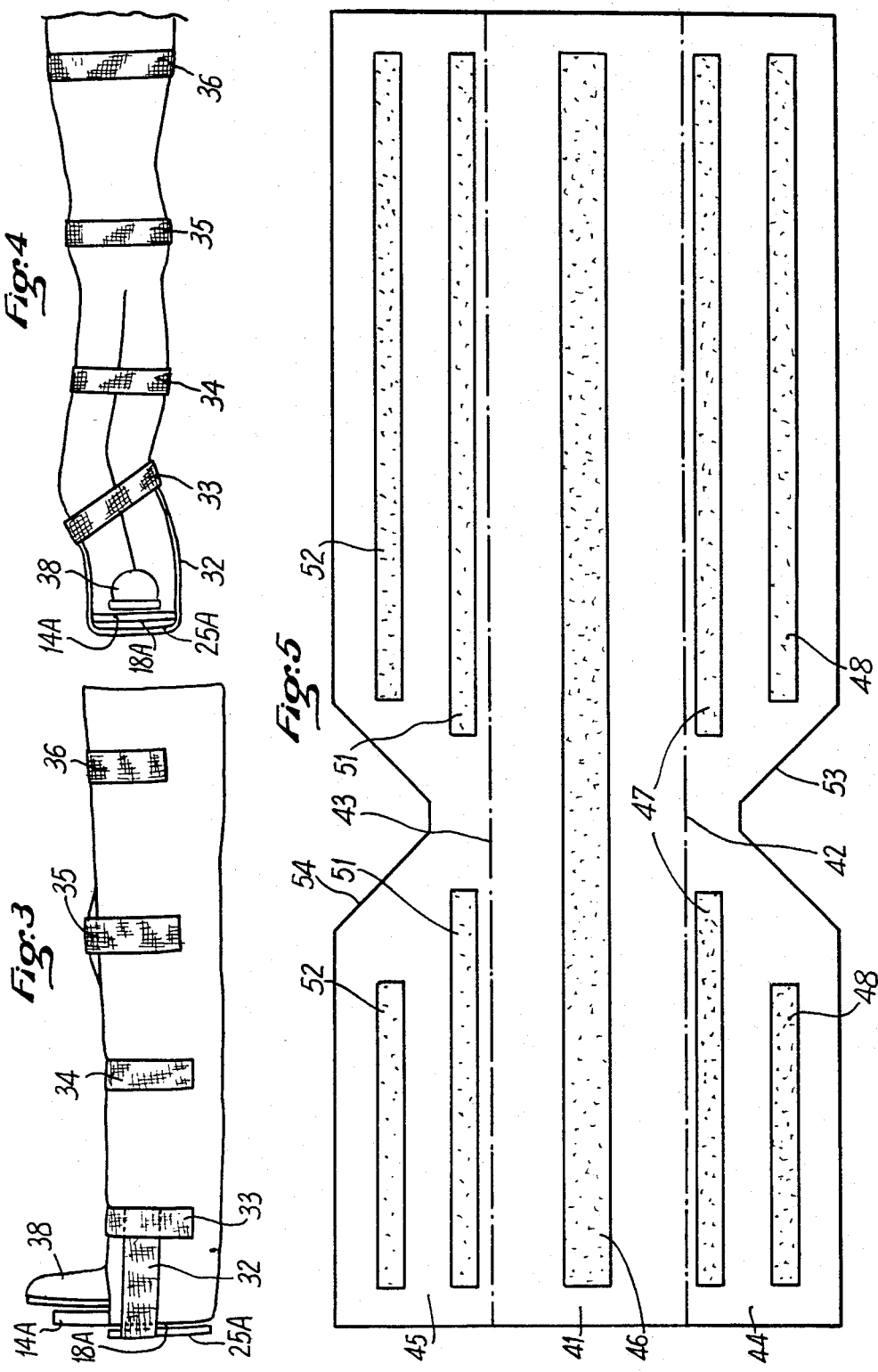

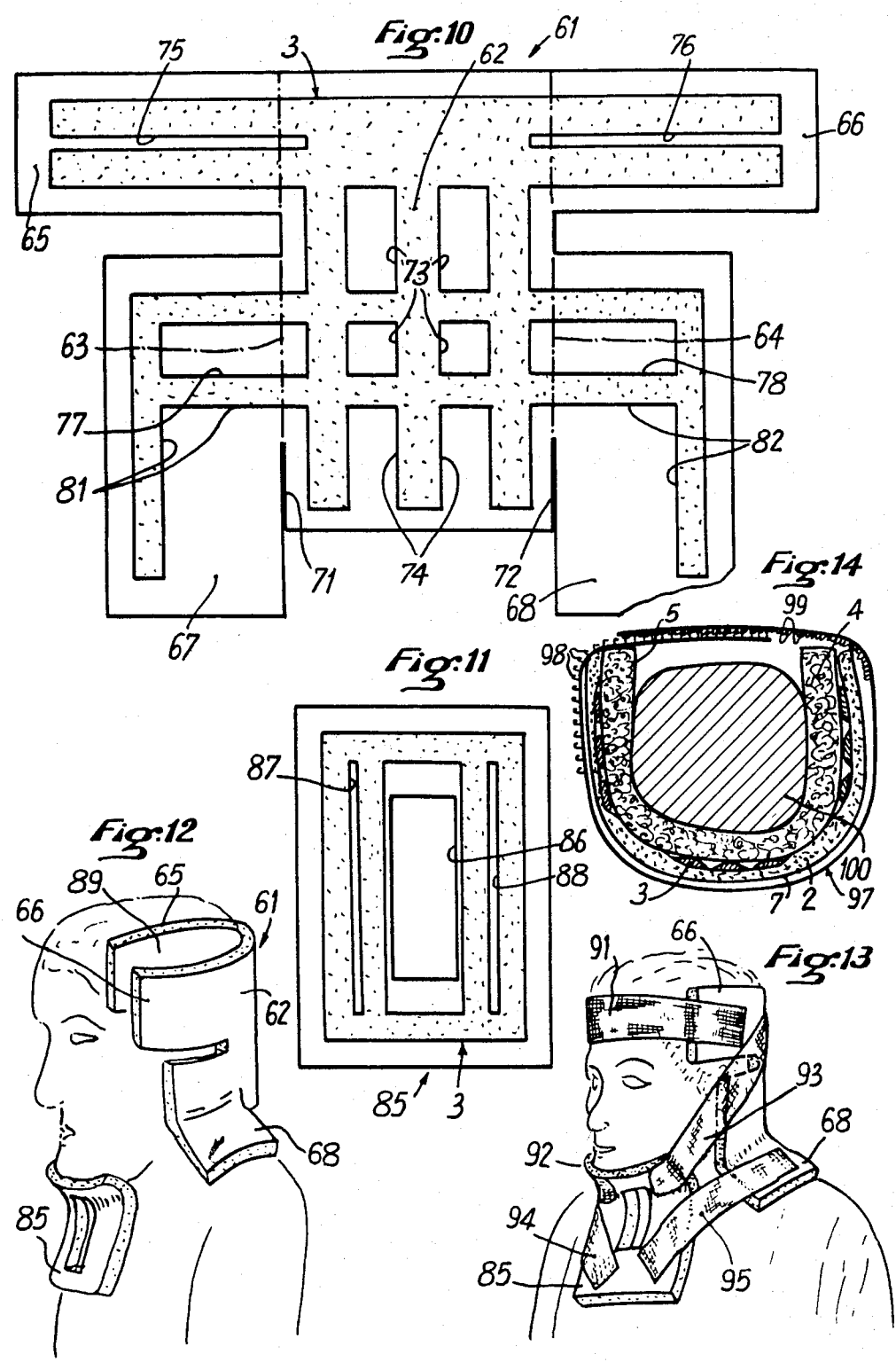

CRADLES AND MINERVA JACKETS, AND MANUFACTURING MATERIAL THEREFOR

The invention relates to articles such as cradles or surgical neck braces for supporting members or the head of persons or animals.

Numerous articles of this kind have long been known, but they present a certain number of drawbacks. Thus for the immobilisation of a fractured leg the Jeanbrau blind is known which comprises parallel wooden slats interconnected like those of a blind and permits the urgent manufacture of an emergency surgical cradle, but it possesses the drawback of being bulky and necessitates the positioning of a padding for the protection of the injured member. Kramer's splint, formed from metallic latticework, is deformable in only one plane and also necessitates a protective padding the positioning of which is quite lengthy; moreover it is opaque to X-rays. The pneumatic splint surrounds the member and effects it immobilisation by the fact that it is inflatable, but it does not permit of giving regard to a deformation and it is relatively fragile. The Metallic cradle formed of latticework necessitates a protective padding, it does not permit of giving regard to a deformation greater than the width of the cradle, and it is opaque to X-rays.

The purpose of the invention is to realise supporting articles which do not possess the above-stated drawbacks of the articles referred to above.

To this end it has first of all for object a new material from which it is possible to manufacture such articles.

This material is characterised in that it is constituted by a layered panel formed by the assembly of a layer of plastic material in the form of hard foam, a sheet of easily deformable but inelastic metal, a layer of plastic material in the form of flexible foam and a flexible and smooth protective internal sheet. The layer of plastic material in the form of hard foam can be covered, either with an external flexible and smooth sheet in which case the articles manufactured from such a material will be supported by means of bands or straps equipped with fixing means (buckles, "Velcro", etc.), or with a material in flexible loops, such as knitted fabric or brushed fabric, and in this case it will then be possible to utilise straps equipped with elements adapted to hook themselves directly into the said looped material.

Most often the panel and especially the metallic sheet which it includes will be cut out in accordance with predetermined shapes corresponding to the conformations of the various articles to be manufactured, various surgical cradles or surgical neck braces for exemple. In any case as will be understood better hereinafter, in the course of the following statement, it is immediately now understood that the material in question permits of manufacturing articles easy to put into position without precise adjustment, by reason of the plasticity of the product which renders it modellable and consequently of great flexibility in use, especially giving regard to significant deformations of a member, possessing an integrated padding, which articles are solid, light, usable on mountains since they are unaffected by cold, reliable during displacements and transparent to X-rays.

The invention will be better understood on reading of the following description and examination of the accompanying drawing which show, by way of examples, the structure of a panel of material according to the invention and several supporting and protective articles manufactured from such a material.

IN THE DRAWINGS

FIG. 1 represents, in section along the line I—I in FIG. 2, a panel for the manufacture of a surgical cradle according to the invention, for a fractured lower member;

FIG. 2 is a section on a larger scale along the line II—II in FIG. 1;

FIG. 3 and 4 are profile and plan views respectively of a surgical cradle manufactured from the panel according to FIG. 1 and 2, modelled and fixed on a fractured lower member;

FIG. 5 represents from the front a panel (the layer of plastic material in the form of flexible foam and the internal protective sheet of which are assumed to be transparent) for the manufacture of a cradle for the support of the zone comprising forearm, elbow and lower arm part;

FIG. 10 and 11 represent respectively two panels (again with the same part assumed to be transparent) for the manufacture of a surgical neck brace;

FIG. 12 shows in perspective the manner of shaping the two panels according to FIG. 10 and 11 for the preparation of a two-part surgical neck brace;

FIG. 13 illustrates in perspective the manner of fixing the surgical neck brace on the patient; and FIG. 14 shows in cross-section another form of embodiment of a cradle.

Figure 6:
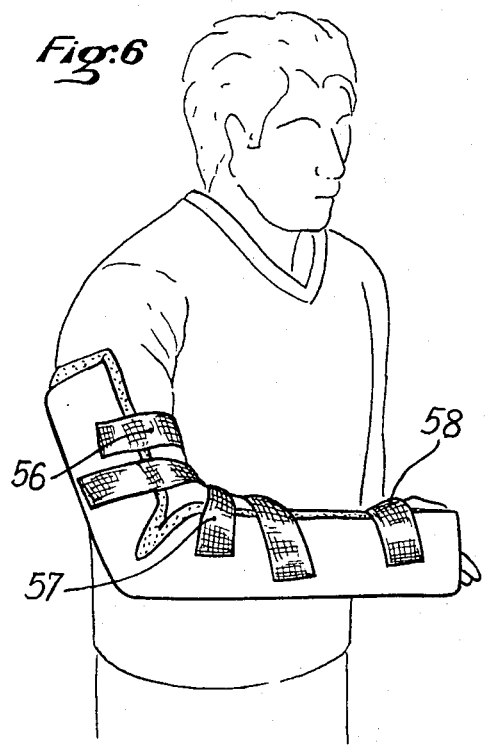
FIG. 6 shows in perspective a cradle manufactured from the panel according to FIG. 5, modelled and fixed on an arm.

The panel 1 as represented in FIG. 1 and 2 is intended for the manufacture of a surgical cradle to be shaped and fixed on a fractured lower member; it is of a layered composite material formed by the assembly of a layer 2 of plastic material in the form of hard foam, a metal sheet 3, preferably inelastic but easily deformable, a layer 4 of plastic material in the form of flexible foam, and a flexible and smooth protective internal sheet 5; moreover the layer 2 of plastic material in the form of hard foam is covered with a material 6 of flexible loops, such as a knitted fabric or a brushed fabric.

The different primary materials utilised are for example the following:

Polyethylene of 5 to 16 mm thickness for the layer 2 of plastic material in the form of hard foam, aluminium for the metallic sheet 3, a mixture of polyurethane and polyester of 20 mm thickness for the layer 4 of plastic material in the form of flexible foam, and a vinyl polychoride for the protective flexible and smooth sheet. The connection between the metallic sheet 3 and the layer 2 of plastic material in the form of hard foam is effected by a self-adhesive glue, for reasons which will be understood better hereinafter.

The metallic sheet 3, of a thickness of the order of 1 mm, is cut into longitudinal strips of about 25 mm width, distinct from one another and substantially parallel, that is to say they have a slight convergence to one of the extremities of the panel which is of generally trapezoidal and almost rectangular form with a base and a height of the order of 42 cm and 1 m respectively; there are found several, three in the example, median longitudinal strips 11, 12, 13 extending over a median longitudinal part 14 of the panel, several, again three in the example, lateral longitudinal strips 15, 16, 17 which extend over a lateral longitudinal part 18 of the panel contiguous with the medial longitudinal part 14 of the latter by a line 19 indicated in dot-and-dash lines, and finally several, again three by symmetry, lateral longitudinal strips 22, 23, 24 extending similarly over a lateral longitudinal part 25 of the panel contiguous with the medial longitudinal part 14 of the panel, on the other side thereof, by a line 26 also indicated in dot-and dash lines. The medial longitudinal metallic strips 11, 12, 13 extend practically over the whole length of the panel, but the lateral longitudinal metallic strips 15, 16, 17 and 22, 23, 24 are shorter at one of their extremities corresponding to the distal extremity of the cradle. The two extreme parts 18A, 25A of the two lateral longitudinal parts 18, 25 of the panel, which are not equipped with metallic strips, are separated from the extreme part 14A of the medial longitudinal part 14 of the said panel respectively by two slots 28, 29 of a length of about 22 cm and they are folded in two upon themselves at the moment of manufacture of the article at works, as indicated at 25B in FIG. 1.

Since the layer 4 of plastic material in the form of flexible foam has an alveolated surface condition limiting the contact surface area, so that it may be glued effectively to the metallic plates 3 and to the parts of the layer 2 of plastic material in the form of hard foam not covered by the said metallic plates, one is induced to spray a neoprene glue on to this flexible foam 4, and on to the adjacent surfaces of the metallic plates and of the layer 2 of plastic material in the form of hard foam, assembly thus being effected glue against glue.

The positioning of the cradle on a fractured lower member is effected easily and permits of giving regard to any deformation of the member; it is slipped beneath the member, the two folded down parts 18A, 25A are raised to a right angle in relation to the plane of the panel, similarly the extreme part 14A of the medial longitudinal part of the panel is raised against the sole of the foot 38 of the injured person, then the two lateral longitudinal parts 18, 25 of the panel are raised and shaped against the sides of the member, the two doubled parts 18A, 25A will pass over the side of the external face of the raised middle part 14A of the panel so as to close the cradle forming a kind of upwardly open box serving as support for the foot. Since the aluminium plates are easily deformable but inelastic, the moulding of the cradle is effected as a function of the deformation of the fracture site and presents no difficulties; so that the cradle may be maintained in place well, it is sufficient to place several straps such as 32, 33, 34, 35, 36 (FIG. 3 and 4) equipped with flexible and elastic elements (of the "Velcro" type for example) forming hooks which attach themselves to the loops of the brushed tissue or knitted fabric which constitutes the outer layer of the cradle. Then it is possible to hook them to any region of the external face of the cradle, which facilitates giving consideration to any deformation.

The layer 2 of plastic material in the form of hard foam evens out the deformations of the aluminium sheet which are the cause of breakage and distributes the modelling over a larger surface area; this property is improved by the presence of the self-adhesive glue discussed above, which permits of re-making the assembly, even if at a given time it should occur that the strips of aluminium and the hard foam are detached from one another over a part of their surface.

The presence of the layer of plastic material in the form of flexible foam of a thickness of 20 mm ensures effective padding, since its density is much lower than that of the external layer of plastic material in the form of hard foam. The internal flexible and smooth protective sheet 5 of vinyl polychloride or smooth-surfaced coated fabric facilitates sliding of the cradle at the time of its positioning and constitutes a protective screen for the foam, facilitating maintenance of the cradle.

Thus the cradle is modelled by hand according to the deformation of the member. A great advantage of this article in comparison with certain flat splints of apparently analogous resides primarily in the equilibrium of the forces of action of the cradle upon the whole of the lower member which is three-quarters wrapped, the resistance of the raised end transverse flap, and the facility of adaptation of the positioning straps to any desired position of the cradle.

In FIG. 5 there may be seen a panel of the same general structure, but adapted to the manufacture of a support cradle for the zone comprising forearm, elbow and lower arm part, the layer of plastic material in the form of flexible foam and the internal protective sheet being assumed to be transparent so that the internal structure of the panel, that is to say the particular cut-out of the metallic sheet, can be seen. The panel, which is rectangular, comprises a median longitudinal part 41 contiguous, by two theoretical straight lines 42, 43 drawn in dot-and-dash lines, with two lateral longitudinal parts 44, 45 respectively. The medial longitudinal part 41 is fitted, over practically its whole length, with a central metallic strip 46. The lateral longitudinal parts 44, 45 are fitted with two metallic strips 47, 48 and 51, 52 which extend also practically over the whole length of the panel, but which display an interruption at an intermediate part of their length, as represented. The panel as a whole presents on its two sides two cut-out parts 53, 54 in line with the said interruptions of the metallic strips respectively. The positions of the interruptions of the metallic strips and of the cut-out parts are such that the cradle as a whole is divided into two parts of unequal lengths, namely:

A short part intended to be placed on the arm (see FIG. 6) and a long part for supporting the forearm, which are connected to one another by the narrow middle part, at the position of the elbow.

The positioning of this cradle is effected under the same conditions as that of the cradle for the lower member as described above, it is modelled according to the deformations of the injured arm and supported by means of straps 56, 57, 58 likewise. The straps are crossed at the level of the forward face of the elbow and permit of immobilising the elbow in the position in which it is accidentally situated. Thus one is not obliged to extend or flex the elbow in order to immobilise it. This cradle is utilisable for the immobilisation of the upper member in the case of osseous or articular lesions affecting the wrist, the forearm, the elbow and the lower third of the arm.

Figure 8:
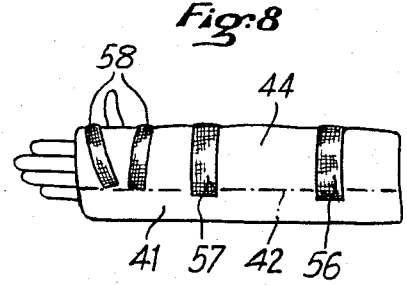
FIG. 8 and 9 are respectively front and plan views of a cradle manufactured from the panel according to FIG. 7, modelled and fixed in the zone of a wrist.
Figure 9:
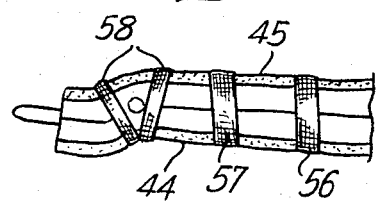
Figure 7:
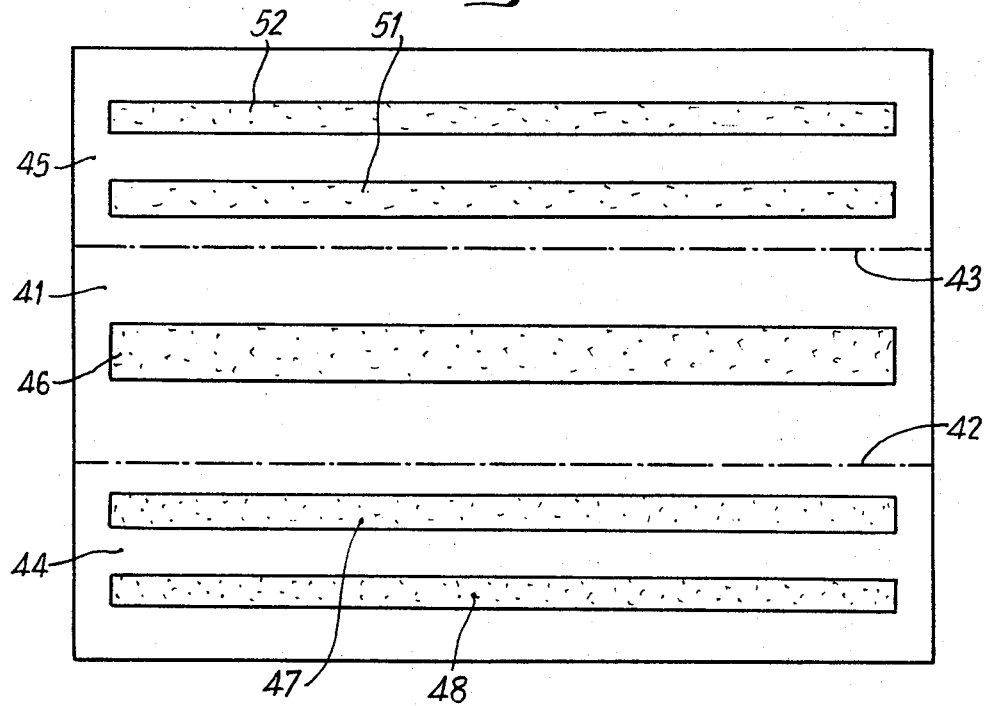
FIG. 7 represents from the front a panel (likewise in which the layer of plastic material in the form of flexible foam and the internal protective sheet are assumed to be transparent) for the manufacture of a cradle for a wrist fracture.

In FIG. 7 there may be seen a panel of the same kind, but a little shorter, without interruptions in the metallic strips and without lateral cut-out portions. In this Figure the same reference numerals have been retained to designate the elements corresponding to those of the form of embodiment according to FIG. 5. As may be seen from FIG. 8 and 9, this type of cradle is utilisable for the immobilisation of the extremity of the upper member in the case of osseous or articular lesions affecting the hand, the wrist and the lower third of the forearm.

In FIG. 10 and 11 there are represented respectively the two elements of a surgical neck brace, that is to say an orthopaedic apparatus intended to keep the head upright. The element according to FIG. 10 is the principal element designated as a whole by 61; it comprises a median part 62 of rectangular form the two lateral limits of which are defined by the two straight lines 63, 64 drawn in dot-and-dash lines, and two rectangular upper lateral wings 65, 66 and two likewise rectangular lower lateral wings 67, 68, all four being contiguous with the median part 62 along the two corresponding abovementioned straight lines 63, 64. The upper edges of the two upper lateral wings 65, 66 are situated at the same level as the upper edge of the median part 62, while in the example the lower edges of the two lower lateral wings are situated a little lower than the lower edge of the median part. Moreover the lower parts of the two lateral edges of the median part 62 are separated from the adjacent part of the two lower lateral wings 67, 68 by slots 71, 72 respectively, in order to facilitate the modelling of the surgical neck brace on the patient. In general this facility is increased by the presence, in all parts of the metallic sheet, of orifices and/or slots of adequate positioning, configuration and dimensions, namely for example: orifices 73 in the central zone of the median part 62, cut-out parts 74 in the lower zone of this same part, slots 75, 76 respectively in the upper lateral wings 65; 66, orifices 77, 78 and very wide cut-out parts 81, 82 in the two lateral lower wings 67, 68 respectively. Moreover in all parts of the metallic sheet the edges of the latter are slightly retracted in relation to the corresponding edges of the panel in order to soften contact of the apparatus upon the skin.

The other element of the surgical neck brace, represented in FIG. 11 is a chin-piece constituted by a simple rectangle 85, again of the same structure as that of the panels discussed hitherto, with a rectangular central orifice 86. The edges of the metallic sheet 3 are also retracted in relation to the corresponding edges of the element and two flexibility slots 87, 88 are provided in the two major sides of the rectangle.

In FIG. 12 there may be seen the manner of utilisation of the surgical neck brace: the modelling of the principal element 61 is effected before the positioning as a function of the position of the head, the other element 85 is applied and takes over from the rescuers hand. The whole is kept in position by means of a front strap 91 which is hooked to the extremities of the two upper lateral wings 65, 66; on each side a strap 92 or 93 passes over the ear obliquely and connects an upper lateral wing 65 or 66 to the corresponding lateral marginal part of the chin-piece 85, while another strap 94 or 95 also connects a lower lateral wing 67 or 68 to the other lateral marginal part of the chin-piece. In other words five straps suffice to retain the whole of the apparatus suitably. The chin-piece permits of maintaining the head at the desired inclination; the orifice 86 (FIG. 11) avoids all compression upon the trachea and leaves swallowing movements free. As for the cradles described above there is no adjustement to be effected in order to position the straps, since they can be hooked to any point of the two elements of the apparatus. The realisation of the apparatus in two elements permits its positioning by two rescuers who at the same time ensure the maintenance of the head and permit evacuation of the injured person with all security.

In FIG. 14 there is represented another form of embodiment of a surgical cradle again manufactured from the same basic material, but the hard plastic foam 2 of which is this time covered not with a material of flexible loops; such as knitted or brushed fabric, as in the forms of embodiment described above, but with a flexible and smooth external sheet 7, for example of coated fabric. In this case straps equipped solely with hook attachment elements obviously could not grip the external smooth surface of the cradle; therefore use will be made for example of straps such as 97 of which one terminal part is equipped with "Velcro" hook elements 98 on its outer face, while its other terminal part is equipped with "Velcro" loop elements 99 on its internal face, so that these two terminal parts grip one another firmly retaining the cradle which they surround. Such a cradle is particularly suitable for the support of a lower member 100 and permits the rescuer to work under difficult conditions, for example in mud, snow or on frozen terrain.

The presented new material, as just stated in several examples, finds direct application in the manufacture of immobilisation devices for urgent rescue work, but it is advantageously also possible to utilise it to manufacture apparatuses for simple protection and support of various parts of the body of men and animals, for example the protection of the legs of horses during transport or training. It is possible to modify the characteristics of its structure as a function of the envisaged applications.

What we claim is:

1. A surgical cradle for supporting the heads or members of persons or animals comprising a layered panel formed by the assembly of a layer of plastic material in the form of hard foam, a sheet of preferably inelastic metal, a layer of plastic material in the form of flexible foam, and a flexible and smooth protective internal sheet, said metal sheet is cut into a predetermined form related to the member being protected.

2. A surgical cradle according to claim 1, characterised in that the distal face of the layer of plastic material in the form of hard foam is covered with a flexible loop material, such as knitted or brushed fabric.

3. A surgical cradle according to claim 1, characterised in that the distal face of the layer of plastic material in the form of hard foam is covered with a flexible and smooth external sheet.

4. A surgical cradle according to claim 3, characterised in that the flexible and smooth external sheet is of coated fabric.

5. A surgical according to claim 1, characterised in that the layer of plastic material in the form of hard foam is of polyethylene.

6. A surgical cradle according to claim 1, characterised in that the metal sheet is of aluminium.

7. A surgical cradle according to claim 1, characterised in that the layer of plastic material in the form of flexible foam is a mixture of polyurethane and polyester.

8. A surgical cradle according to claim 1, characterised in that the flexible and smooth internal protective sheet is of vinyl polychloride.

9. A surgical cradle according to claim 1, characterised in that the connection between the metal sheet and the layer of plastic material in the form of hard foam is affected by a self-adhesive glue.

10. A surgical cradle according to claim 1, wherein the metal sheet is cut into longitudinal strips which are substantially parallel and distinct from one another.

11. Cradle according to claim 10, characterised in that, intended to protect a lower member, it comprises a medial longitudinal part fitted with metal sheet strips over its whole length and two lateral longitudinal parts contiguous with the said median longitudinal part and of the same length as the latter, also fitted with metal sheet strips the length of which, at one of their extremities, is shorter than that of the metallic sheet strips of the median longitudinal part, the parts not fitted with metallic sheet strips of the said lateral longitudinal strips of the material being each separated from the medial longitudinal part by a slot so that they can be applied against the adjacent extremity of the median longitudinal part of the material raised at right angles against the sole of the foot pertaining to the member against which the cradle assembly will be rolled.

12. Cradle according to claim 10, characterised in that, intended to be placed upon a forearm, the elbow and the lower part of the arm, it comprises a median longitudinal part fitted with metallic sheet strips over its entire length and two lateral longitudinal parts contiguous with the said median longitudinal part and of the same length as the latter, fitted with metallic sheet strips which have an interruption on an intermediate part of their length, the panel assembly having on each side a cut-out part in line with the said interruption of the metallic sheet strips.

13. Surgical protective neck brace, characterised in that it is manufactured from a material according to claim 1 and comprises two elements, namely: a principal element and a chin-piece, the principal element comprising a median part of rectangular form with two upper lateral wings intended to be turned forward against the temples and two lower lateral wings intended to be modelled against the sides of the head and over the top of the shoulders, while the chin-piece is constituted by a simple rectangular element having a central orifice, the metallic sheet, in all the parts of the two elements of the neck brace, being orificed and/or slotted in places to facilitate their shaping.

14. A surgical cradle according to claim 2, wherein for use as a protective neckbrace the metal sheet of which is cut out in a predetermined form corresponding to the conformation of the neck brace, the said neck brace comprising on the one hand two elements, namely: a principal element and a chin-piece, the principal element comprising a median part of rectangular form with two upper lateral wings intended to be turned forward against the temples and two lower lateral wings intended to be modelled against the sides of the head and over the top of the shoulders, while the chin-piece is constituted by a simple rectangular element having a central orifice, the metallic sheet, in all parts of the two elements of the neck brace, being orificed and/or slotted in places to facilitate their shaping, and furthermore straps equipped with elements for hooking into the looped material covering the two constituent elements of the neck brace.

15. A surgical cradle according to claim 14, comprising five fastening straps, namely: a forehead strap which is hooked to the extremities of the two upper lateral wings and on each side a lateral strap which hooks itself to the corresponding lower lateral wing and to the corresponding marginal part of the chin-piece, and another lateral strap which passes over the ear of the patient and is hooked to the corresponding upper lateral wing and to the corresponding marginal part of the chin-piece.

16. A surgical cradle according to claim 2, wherein for protecting a member the metal sheet is cut into longitudinal strips which are substantially parallel and distinct from one another, and in that it is equipped with straps equipped with elements for hooking into the flexible looped material covering the distal face of the layer of plastic material in the form of hard foam of the said material.

17. A surgical cradle according to 16, wherein the metal sheet is cut into longitudinal strips which are substantially parallel and distinct from one another, and in that it is equipped with straps equipped with means for mutual hook attachment of their terminal parts.

* * * * *